United States Patent
Chen et al.

(10) Patent No.: US 7,052,783 B2
(45) Date of Patent: May 30, 2006

(54) OXADIAZOLE TETRAMERS

(75) Inventors: Chin-Ti Chen, Taipei (TW); Hsiu-Chih Yeh, Taipei (TW); Li-Hsin Chan, Taoyuan (TW); Rong-Ho Lee, Chiai (TW)

(73) Assignee: Academia Sinica, Taipei (TW)

( * ) Notice: Subject to any disclaimer, the term of this patent is extended or adjusted under 35 U.S.C. 154(b) by 422 days.

(21) Appl. No.: 09/996,202

(22) Filed: Nov. 28, 2001

(65) Prior Publication Data

US 2002/0102433 A1    Aug. 1, 2002

Related U.S. Application Data

(60) Provisional application No. 60/253,605, filed on Nov. 28, 2000.

(51) Int. Cl.
*H05B 33/12* (2006.01)
*C09K 11/08* (2006.01)

(52) U.S. Cl. .................... 428/690; 428/917; 313/504; 313/506; 544/179; 544/180; 548/110; 548/125; 548/131; 548/146; 548/215; 548/250; 548/300.1; 556/413; 556/465

(58) Field of Classification Search ................ 428/690, 428/917; 252/301.16; 313/503, 504, 506; 548/143, 145, 235, 250; 556/413
See application file for complete search history.

(56) References Cited

U.S. PATENT DOCUMENTS

| | | | | |
|---|---|---|---|---|
| 5,336,546 A | * | 8/1994 | Hironaka et al. | 428/209 |
| 5,343,050 A | * | 8/1994 | Egusa et al. | 257/40 |
| 5,840,217 A | | 11/1998 | Lupo et al. | 252/583 |
| 5,859,211 A | | 1/1999 | Kreuder et al. | 528/403 |
| 6,391,482 B1 | * | 5/2002 | Matsuo et al. | 428/690 |

FOREIGN PATENT DOCUMENTS

EP    WO00/03565    *   1/2000

OTHER PUBLICATIONS

Salbeck, et al. *Low molecular organic glasses for blue electroluminescence*. Synthetic Metals, vol. 91, 1997, pp. 209-215.
Weinfurtner, et al. *Novel amorphous molecular materials for organic light-emitting devices*. SPIE, vol. 3476, Jul. 1998, pp. 40-48.
Salbeck, et al. *Spiro Linked Compounds For Use As Active Materials In Organic Light Emitting Diodes*. Macromol. Symp. vol. 125, 1997, pp. 121-132.
Oldham, Jr., et al. *Synthesis, Spectroscopy, and Morphology of Tetrastilbenoidmethanes*. J. Am. Chem. Soc., vol. 120, 1998, pp. 2987-2988.
Wang, et al. *Synthesis, Morphology, and Optical Properties of Tetrahedral Oligo(phenylenevinylene) Materials*. J. Am. Chem Soc., vol. 122, 2000, pp. 5695-5709.

* cited by examiner

*Primary Examiner*—Rena Dye
*Assistant Examiner*—Camie S. Thompson
(74) *Attorney, Agent, or Firm*—Fish & Richardson PC

(57) ABSTRACT

This invention relates to tetraphenylmethane-based oxadiazole molecules that act as electron transporting materials to be used in electroluminescent devices. The oxadiazole compounds are of the following formula. Each variable is defined in the specification.

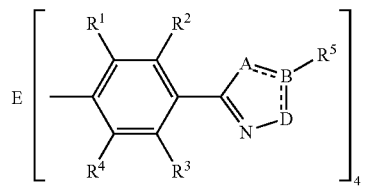

18 Claims, No Drawings

OXADIAZOLE TETRAMERS

RELATED APPLICATIONS

This application claims priority to U.S. provisional application No. 60/253,605, filed on Nov. 28, 2000, the contents of which are incorporated herein by reference.

BACKGROUND

Electroluminescent (EL) devices based on organic thin layers have recently attracted much attention because of their potential uses in large-area flat-panel displays and light-emitting diodes (LED). Organic LEDs (OLEDs) have been made with both low molecular-weight organic materials and with polymers. The performance of these devices is significantly influenced by the charge balance between electrons and holes from opposite electrodes. The charge can be balanced by using a bilayer structure including a hole transport layer and an electron transport layer. One or both of these layers can be luminescent.

An important quality of organic EL materials is their durability, i.e., thermal and morphological stability. Thus, it is desirable that organic EL materials are not only light-emitting and hole-transporting, but also robust. In addition, it is desirable that an amorphous (glassy) thin film remain homogenous without crystallization or coagulation under the high temperatures reached during operation of the OLED.

SUMMARY

This invention relates to tetraphenylmethane-based molecules that act as electron transporting materials.

In one aspect, the invention features a compound of the following formula:

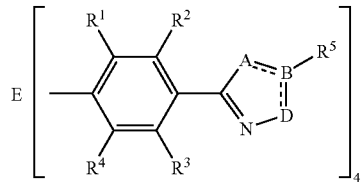

where each of $R^1$–$R^4$ is, independently, H, substituted or unsubstituted $C_{1-6}$ alkyl, OH, $C_{1-6}$ alkoxy, or $N(R^6)(R^7)$. For $N(R^6)(R^7)$, each of $R^6$ and $R^7$ is, independently, H or substituted or unsubstituted $C_{1-6}$ alkyl.

Each of $R^1$–$R^4$ can also be $NO_2$, CN, or $CO_2R^8$, in which $R^8$ is H or $C_{1-6}$ alkyl.

$R^5$ is H, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{6-20}$ aryl, substituted or unsubstituted alkylaryl, substituted or unsubstituted $C_{4-20}$ heteroaryl, $C_{10-20}$ diarylaminoaryl, or is absent. Alternatively, B and D, together with $R^5$ and $R^{11}$, are substituted or unsubstituted aryl.

A is O, S, or $N(R^9)$. $R^9$ may be absent, H, substituted or unsubstituted alkyl, or substituted or unsubstituted aryl. A may also be N=N, or $N=C(R^{10})$ in which the C is adjacent to B and in which $R^{10}$ is substituted or unsubstituted alkyl, or substituted or unsubstituted aryl.

B is C or N. D is N, NH, or $C(R^{11})$ in which $R^{11}$ is substituted or unsubstituted alkyl, or substituted or unsubstituted aryl, or B and D, together with $R^5$ and $R^{11}$, are substituted or unsubstituted aryl.

E is C or Si.

In this compound, when A is O and D is N, then B is C and the floating double bond is between B and D. When A is $N(R^9)$ and $R^9$ is absent, then B is N, $R^5$ is absent, D is NH, and the floating double bond is between A and B. When A is N=N, then B is C, D is N, and the floating double bond is between B and D. When A is $N=C(R^{10})$, then B is N, $R^5$ is absent, D is $C(R^{11})$, and the floating double bond is between B and D. When A is $N(R^9)$ and $R^9$ is H, alkyl, or aryl, then B is C, D is $C(R^{11})$, and the floating double bond is between B and D. Finally, when A is O or S and D is $C(R^{11})$, then B is C and the floating double bond is between B and D.

In preferred embodiments, A is O. In other preferred embodiments, each of $R^1$–$R^4$ is H. In other preferred embodiments, $R^5$ is substituted or unsubstituted aryl, or substituted or unsubstituted alkylaryl. For example, $R^5$ may have the following formula:

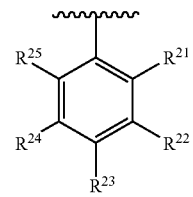

wherein each of $R^{21}$–$R^{25}$ is, independently, H, substituted or unsubstituted $C_{1-6}$ alkyl, OH, $C_{1-6}$ alkoxy, or $N(R^{26})(R^{27})$, in which each of $R^{26}$ and $R^{27}$ is, independently, H, substituted or unsubstituted $C_{1-6}$ alkyl, substituted or unsubstituted aryl, or substituted or unsubstituted alkylaryl. Each of $R^{21}$–$R^{25}$ may also be $NO_2$, CN, or $CO_2R^{28}$, in which $R^{28}$ is H or $C_{1-6}$ alkyl. In this compound, each of $R^{21}$–$R^{25}$ preferably is, independently, H, methoxy, tert-butyl, or trifluoromethyl.

In other preferred embodiments, A is $N(R^9)$, in which $R^9$ is absent.

The term "saturated" used herein refers to a compound or portion of a compound having each atom either hydrogenated or substituted such that the valency of each atom is filled.

The term "unsaturated" used herein refers to a compound or portion of a compound where the valency of each atom may not be filled with hydrogen or other substituents. For example, adjacent carbon atoms can be doubly bound to each other.

The term "substituted" used herein refers to moieties having one, two, three or more substituents, which may be the same or different, each replacing a hydrogen atom. Examples of substituents include but are not limited to alkyl, hydroxyl, protected hydroxyl, amino, protected amino, carboxy, protected carboxy, cyano, alkoxy, halo, and nitro.

The term "unsubstituted" used herein refers to a moiety having each atom hydrogenated such that the valency of each atom is filled.

The term "aryl" used herein refers to a moiety having a hydrocarbon ring system (e.g., a fused ring system) having at least one aromatic ring. Examples of aryl moieties include, but are not limited to, phenyl, naphthyl, and pyrenyl.

The term "heteroaryl" used herein refers to a moiety having a ring system (e.g., a fused ring system) with at least one aromatic ring and at least one heteroatom, including, but not limited to, O, N, and S. Examples of heteroaryl moieties include, but are not limited to, pyridinyl, carbazolyl, and indolyl.

Protected forms of the compounds described herein are included within the scope of the invention. In general, the species of protecting group is not critical, provided that it is stable to the conditions of any subsequent reaction(s) on other positions of the compound and can be removed at the appropriate point without adversely affecting the remainder of the molecule. In addition, one protecting group may be substituted for another after substantive synthetic transformations are complete. Examples and conditions for the attachment and removal of various protecting groups are found in T. W. Greene, Protective Groups in Organic Chemistry, (1st ed., 1981, 2nd ed., 1991).

In addition, salts of the compounds described herein are within the scope of the invention. For example, a salt can be formed between a positively charged amino substituent and a negatively charged counterion.

Four exemplary compounds of this invention are:
tetrakis(4-(5-(3,4-dimethoxyphenyl)-2-oxadiazolyl)phenyl) methane (OMEOXD), tetrakis(4-(5-(3,5-di-tert-butylphenyl)-2-oxadiazolyl)phenyl)methane (TBUOXD),

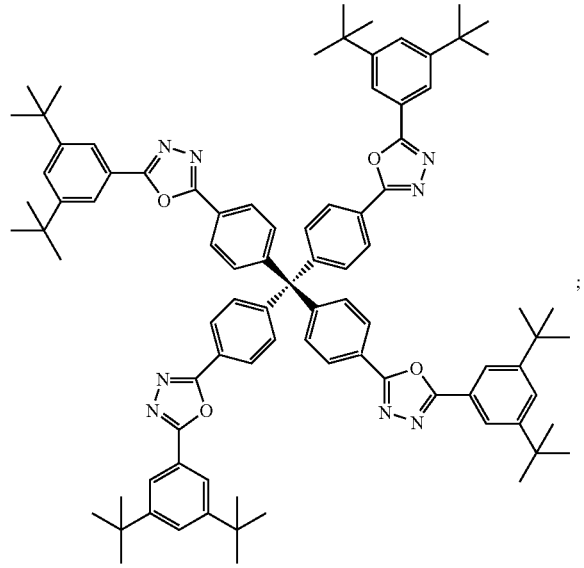

tetrakis(4-(5-(3-(a,a,a-trifluoromethylphenyl))-2-oxadiazolyl)phenyl)methane (CF3OXD),

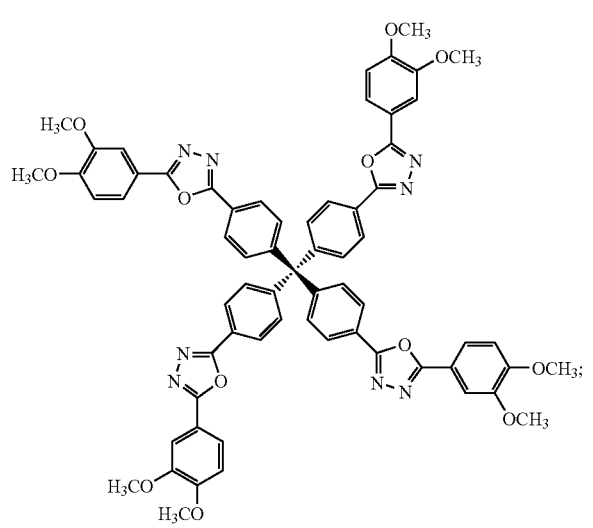

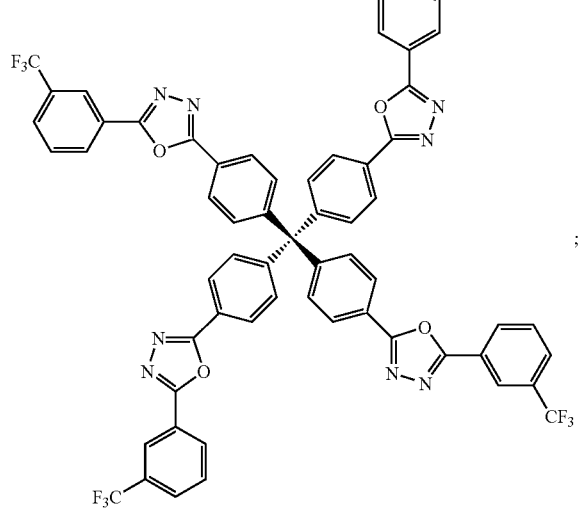

tetrakis(4-(5-(4-diphenylaminophenyl)-2-oxadiazolyl)phenyl)methane (p-TPAOXD),

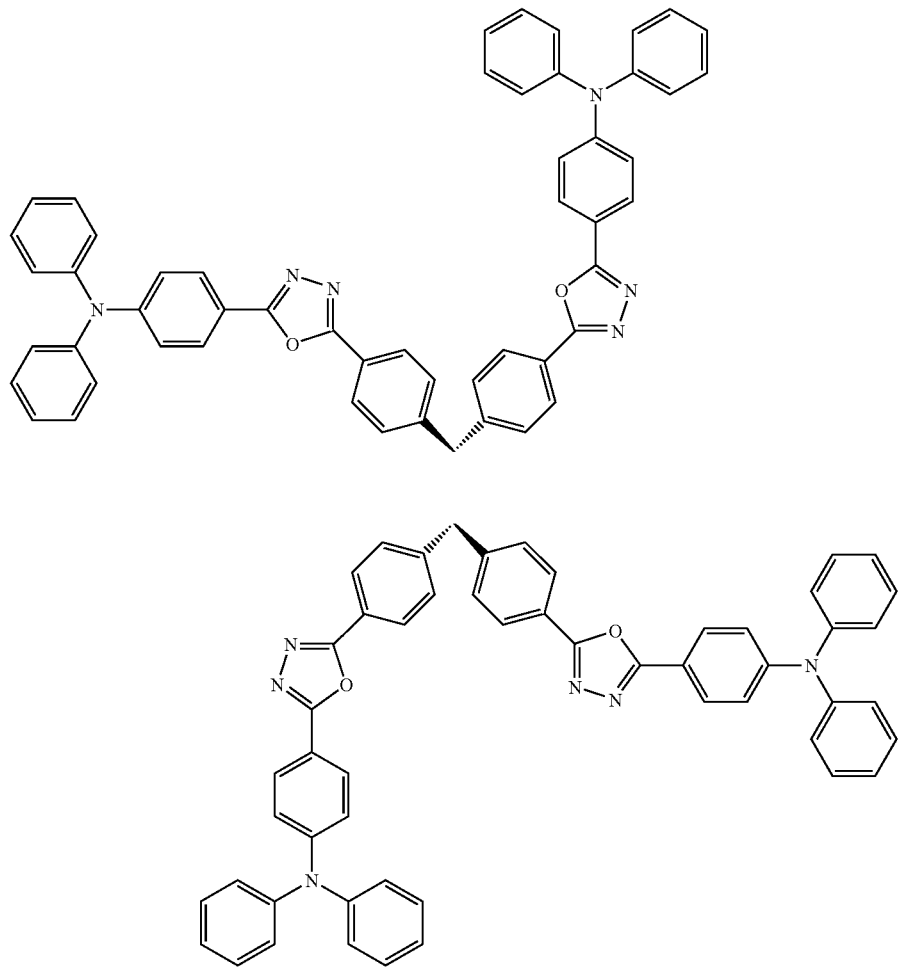

DETAILED DESCRIPTION

The invention features tetraphenylmethane-based compounds and OLED devices made using these compounds. For example, the invention features tetraphenylmethane-based 1,3,4-oxadiazole compounds. These compounds can help improve the physical properties of the organic LEDs into which they are incorporated.

A method for synthesizing a tetraphenylmethane oxadiazole compound is as follows: A tetrakis (4-substituted-phenyl)methane is allowed to react with a desired substituted aryl or heteroaryl compound. The phenyl groups of the tetrakis (4-substituted-phenyl)methane may be functionalized with, for example, halo, cyano, or acyl halide. These groups react with functional groups on the aryl or heteroaryl compounds. Examples of such functional groups include, for example, amines, hydroxyls, and tetraazolyls. Alternatively, a tetrakis-(4-cyanophenyl)methane can be converted to a tetrakis-4-(tetraazolylphenyl)methane compound, and the tetraazolyl compound can be combined with various acid chlorides to form tetrahedral oxadiazole compounds. Syntheses for various compounds are described in more detail in the Examples, below.

Tetrahedral oxadiazole derivatives are useful as organic EL materials for a variety of reasons. The multiple-branch design of the oxadiazole tetramers results in increased melting temperatures. In addition, these compounds have amorphous characteristics, despite their highly symmetrical molecular frameworks. The glass transition temperatures ($T_g$s) of these compounds, which are commonly used as stability indicators for the amorphous states, are generally high. Furthermore, the compounds are thermally robust; amorphous glassy thin films of these compounds remain homogenous without crystallization or coagulation under the heating conditions used during OLED operation. The compounds also display stable external quantum efficiencies.

In another aspect, the invention features an electroluminescence device comprising a substrate, a hole transporting layer, an emitting layer, and an electron transporting layer, wherein at least one of the hole transporting layer, the emitting layer, and the electron transporting layer comprises one or more the tetraphenylmethane-based compounds of this invention.

The details of one or more embodiments of the invention are set forth in the description below. Other features, objects, and advantages of the invention will be apparent from the description, and from the claims.

The compounds of the invention can be used to make electroluminescence devices. A diagrammatic representation of such a device is shown below.

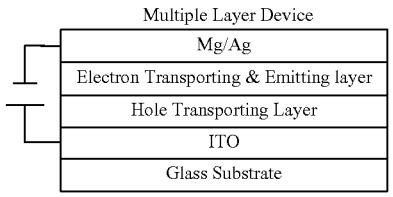

Electroluminescence devices can include multiple layers, or they can be composed of a single layer. A typical multi-layer device includes a substrate, e.g., glass, which may be coated with an oxide, e.g., indium-tin-oxide (ITO). The device also includes a hole transporting layer, an electron transporting layer, and an emitting layer. The hole transporting layer and the emitting layer may be combined into a single layer, or the emitting layer and the electron transporting layer may be combined into a single layer. Alternatively, the hole transporting layer, the electron transporting layer, and the emitting layer can all be combined into a single layer; such a device is referred to herein as a single layer device. The device may also include a cathode.

Devices can be prepared by vacuum deposition of any of the compounds described herein as hole transporting layer, followed by $Alq_3$ as the emitting layer and the electron-transporting layer. $Alq_3$ (tris(8-quinolinolato)aluminum (III)) is described in C. W. Tang, S. A. VanSlyke, *Appl. Phys. Lett.* 1987, 51:913; J. Kido, Y. Lizumi, *Chem. Lett.* 1997, 963. The layers are deposited on an indium-tin-oxide (ITO) coated glass substrate. For single layer devices, the $Alq_3$ layer is omitted, and the oxadiazole compound serves as the hole transporting, emitting, and electron transporting layer. An alloy of magnesium and silver (ca. 8:1, 500 Å), which serves as the cathode, can be deposited onto the organic layer by simultaneously evaporating from two different sources. The cathode is capped with 1000 Å of silver.

Without further elaboration, it is believed that one skilled in the art can, based on the description herein, utilize the present invention to its fullest extent. All publications recited herein are hereby incorporated by reference in their entirety. The following specific examples, which describe the syntheses of various compounds and devices of the invention, are therefore to be construed as merely illustrative, and not limitative of the remainder of the disclosure in any way.

EXAMPLE 1

Synthesis of Tetrakis(4-tetraazolylphenyl)methane (Compound 2)

Tetrakis(4-cyanophenyl)methane (5.00 g, 11.90 mmol) was added to $NaN_3$ (4.65 g, 71.35 mmol) and ammonium chloride (3.82 g, 71.35 mmol) in dried DMF (25 mL). It was then slowly heated up to 100° C. for 24 hours under nitrogen. After the reaction mixture cooled down, it was acidified with 2 N HCl(aq) with adequate amounts of water until acidic conditions were reached, and a white powder slowly appeared. The product was isolated by filtration and washed thoroughly with water to eliminate excess salts. The product was dried in the present of $P_2O_5$ in a vacuum oven.

Yield: 96% (6.85 g). $^1$H NMR (300 MHz, $d_6$-DMSO): δ [ppm] 7.54 (d, 8H, J=8.5 Hz), 8.02 (d, 8H, J=8.5 Hz). $^{13}$C{1H} NMR (75 MHz, $d_6$-DMSO): δ [ppm] 155.0, 148.3, 131.2, 127.0, 122.4, 64.9. FAB-MS: calcd MW, 592.21, m/e=592 ($M^+$). Anal. Found (calcd) for $C_{29}H_{20}N_{16} \cdot 2H_2O$: C, 55.41(55.44); H, 3.80(3.85); N, 35.31(35.68).

EXAMPLE 2

Synthesis of Tetrakis(4-(5-(3,4-dimethoxyphenyl)-2-oxadiazolyl)phenyl)methane OMEOXD (Compound 3)

Tetrakis(4-tetraazolylphenyl)methane (Compound 2) (1.18 g, 2.0 mmol) was dissolved in dried anisole (50 ml) containing 3,4-dimethoxybenzyloyl chloride (1.76 g, 8.8 mmol). 2,4,6-Collidine (1.2 mL) was added dropwise to the mixture with stirring. After the addition of collidine, the solution was stirred for 3 hours at about 110° C. under nitrogen atmosphere. During the stirring, white precipitates gradually emerged. The solution was subjected to flash column chromatography (silica gel, 19 parts of chloroform vs. 1 part ethyl acetate). The first bright purplish blue band (under long-wavelength UV light) that developed was collected.

Yield: 50% (1.09 g). $^1$H NMR (300 MHz, $CDCl_3$): δ [ppm] 8.10 (d, 8H, J=8.3 Hz) 7.65 (d, 4H, J=8.4 Hz). 7.64 (s, 4H), 7.47 (d, 8H, J=8.3 Hz) 6.97 (d, 4H, J=8.4 Hz), 3.97 (s, 12H), 3.94 (s, 12H). $^{13}$C{1H} NMR (75 MHz, $CDCl_3$): δ [ppm] 165, 164, 152, 149, 148, 131, 127, 122, 120, 116, 111, 110, 65, 56. FAB-MS: calcd MW, 1136.37.21, m/e=1136 ($M^+$). Anal. Found (calcd) for $C_{65}H_{58}N_8O_{15}$ (3.3$H_2O$): C, 66.17(65.53); H, 4.88(4.91); N, 8.25(9.41).

EXAMPLE 3

Tetrakis(4-(5-(3,5-di-tert-butylphenyl)-2-oxadiazolyl)phenyl)methane TBUOXD (Compound 4)

Tetrakis(4-tetraazolylphenyl)methane (Compound 2) (0.89 g, 1.5 mmol) was reacted with 3,5-di-tert-butyl benzoyl choloride (1.70 g, 6.6 mmol) in the same manner as in the synthesis of Compound 3. The first bright blue band (under long-wavelength UV light) that developed during flash column chromatography (silica gel, 9 part dichloromethane vs. 1 part ethyl acetate) was collected.

Yield: 70% (1.40 g). $^1$H NMR (300 MHz, $CDCl_3$): δ [ppm] 8.14 (d, 8H, J=8.6 Hz), 7.94 (d, 8H, J=1.5 Hz), 7.60 (t, 4H, J=1.5 Hz), 7.50 (d, 8H, J=8.6 Hz), 1.37 (s, 72H). $^{13}$C{1H} NMR (75 MHz, $CDCl_3$): δ [ppm] 166, 164, 152, 149, 131, 127, 126, 123, 122, 121, 66, 35, 31. FAB-MS: calcd MW, 1344.79, m/e=1344 ($M^+$). Anal. Found (calcd) for $C_{29}H_{24}N_{16}O_2$ (4.2$H_2O$): C, 77.13(77.36); H, 7.35(7.59); N, 7.85(8.11).

EXAMPLE 4

Tetrakis(4-(5-(3-(a,a,a-trifluoromethylphenyl))-2-oxadiazolyl)phenyl)methane CF3OXD (Compound 5)

Tetrakis(4-tetraazolylphenyl)methane (Compound 2) (2.69 g, 5.0 mmol) was reacted with 3-(trifluoromethyl)benzoyl choloride (3.3 mL, 22.0 mmol) in the same manner as in the synthesis of Compound 3. The first bright blue band (under long-wavelength UV light) that developed during flash column chromatography (silica gel, 6 part dichloromethane vs. 1 part ethyl acetate) was collected.

Yield: 92% (5.40 g). $^1$H NMR (300 MHz, CDCl$_3$): δ [ppm] 8.35 (s, 4H), 8.33 (d, 4H, J=8.2 Hz), 8.15 (d, 8H, J=8.4 Hz), 7.89 (d, 4H, J=8.2 Hz), 7.68 (t, 4H, J=8.2 Hz), 7.51 (d, 8H, J=8.4 Hz). $^{13}$C{1H} NMR (75 MHz, CDCl$_3$): δ [ppm] 164, 163, 149, 132 (q JCF=33 Hz), 131, 130, 129, 128, 127, 125, 124, 123 (q, JCF=271 Hz), 122, 66. FAB-MS: calcd MW, 1168.24, m/e=1169 (M+1$^+$). Anal. Found (calcd) for $C_{61}H_{32}F_{12}N_8O_4$: C, 62.01 (62.68.44); H, 2.67(2.76); N, 9.10(9.59).

The syntheses of compounds 2–5 are shown below in Scheme 1.

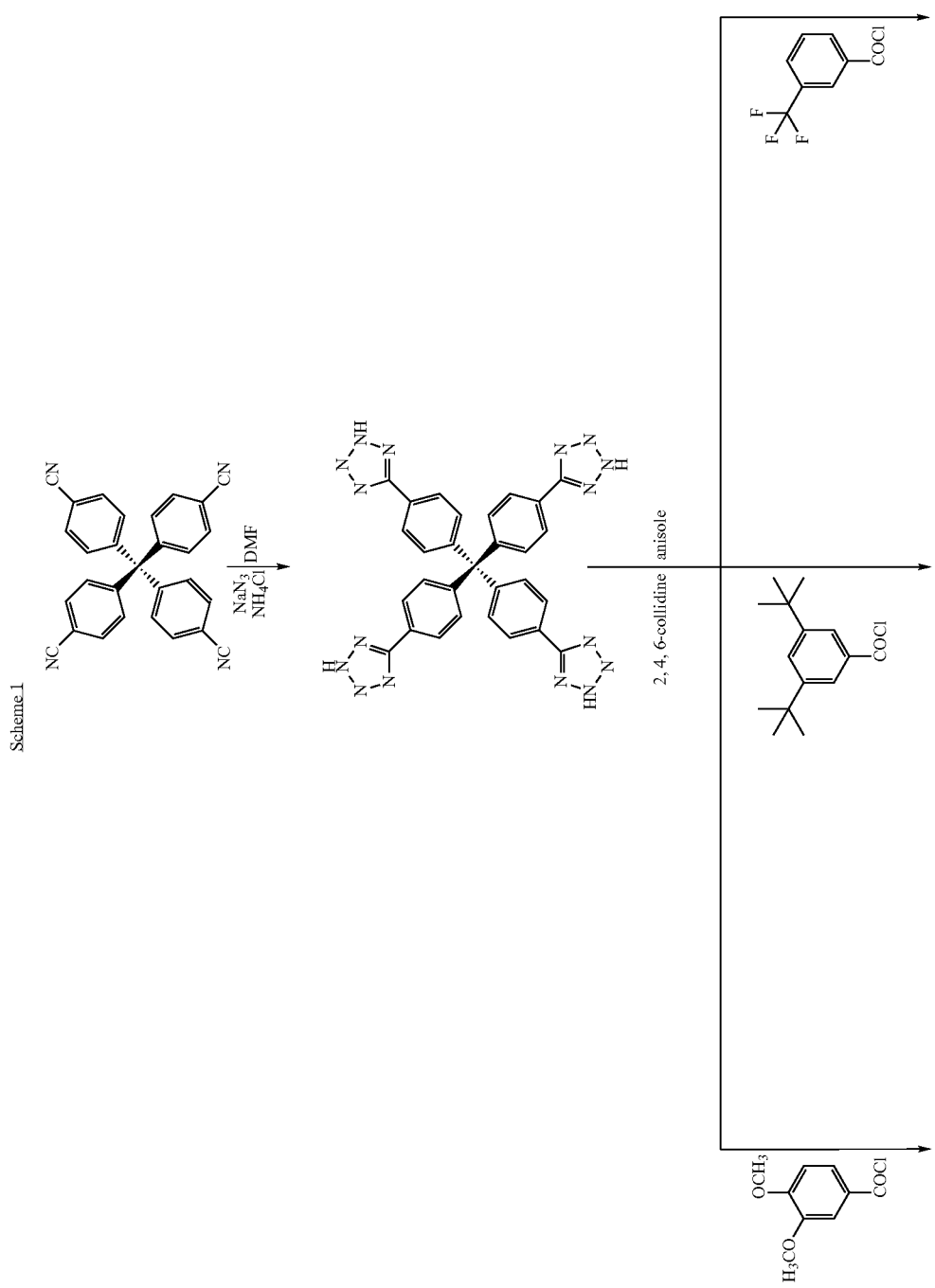

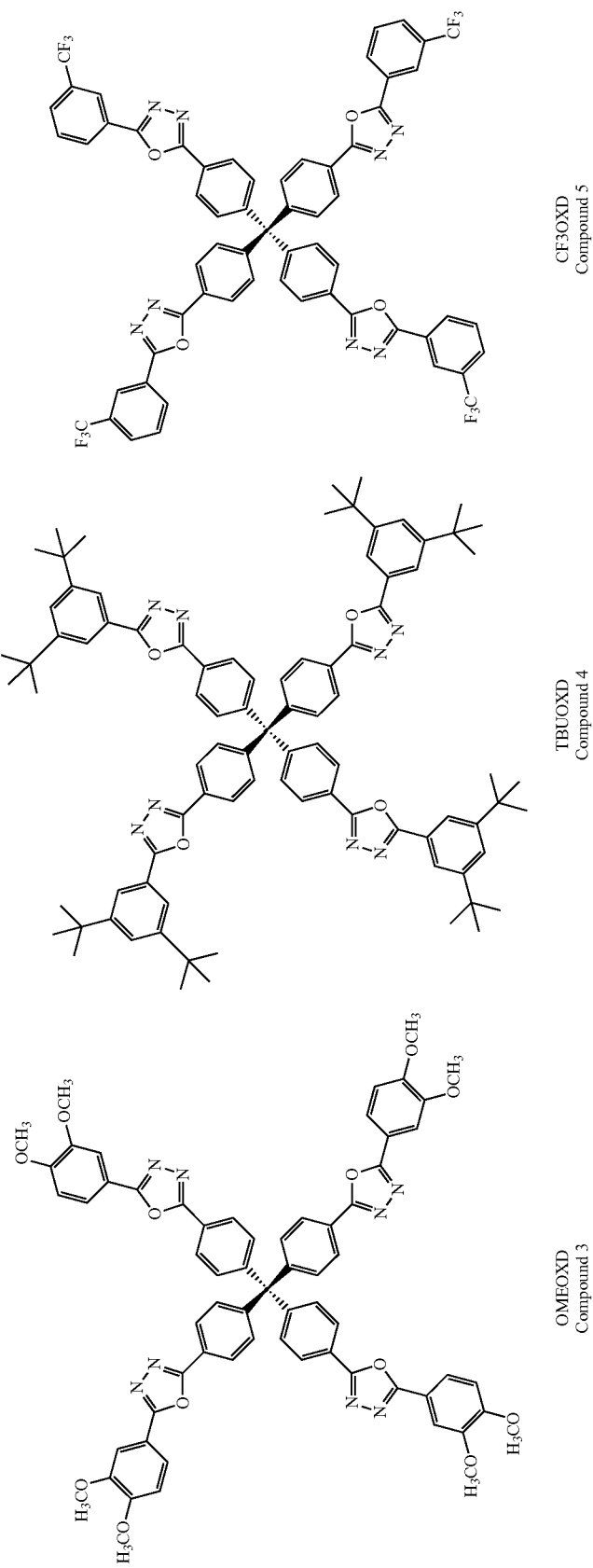

EXAMPLE 5

Physical and Electronic Properties of Compounds 3–5

Compounds 3–5 were either white or off-white solids with absorption maxima ($\lambda_a$) in a narrow range of 292–315 nm in solution, as shown in Table 1. Among 3–5, the smallest shift (blue shifted with 7 nm) of $\lambda_a$ compared to that of PDB (2-(4-biphenylyl)-5-(4-tert-butylphenyl)-1,3,4-oxadiazole, an electron-transporting compound) was found for 4, which has a tert-butyl substituent on the meta position that hardly affects the electronic state of the oxadiazole ring. These spectroscopic observations indicated that the tetrameric tetrahedron framework had no or little effect on the π-conjugation system of oxadiazole molecules. The π-systems of the four 2-aryl-1,3,4-oxadiazole units of compounds 3–5 seemed to interact with each other, in spite of a nonplanar sp³-hybridized carbon in between.

Compounds 3–5 fluoresced purplish blue (4 and 5) to blue (3) both in solution and in the solid-state. The fluorescence quantum efficiencies ($\Phi_F$) of 3–5 and PBD in solution were determined, as shown in Table 1. They were all comparable to $\Phi_F$=0.8~0.9. Although $\lambda_a$ randomly varied with respect to that of PBD, 3–5 all had fluorescence maximums ($\lambda_f$) about 10 to 25 nm red-shifted relative to that of PBD (see Table 1).

Cyclic voltammetry measurements showed that compounds 3–4, as well as PBD, had either quasi reversible or irreversible votammograms with comparable potentials of the first reduction process (see Table 1). The potential of the first reduction process of 5 was considerably low at –1.32 eV. This may be attributed to the reduction of α,α,α-trifluorotoluene instead of the oxadiazole ring (the reduction potential of α,α,α-trifluorotoluene was determined to be –1.34 eV).

The cyclic voltammetry data imply that the tetraphenylmethane framework and peripheral substituents do not significantly alter the electron-capture tendency of the oxadiazole rings in 3–5 compared with that of PBD.

Although similar in spectroscopic and electrochemical behavior, tetraphenylmethane-based oxadiazaole 3–5 had very different thermal properties when compared with PBD. In DSC measurements, a distinct endothermic peak at 137° C. was observed, which corresponds to the melting temperature of PBD. The crystallization temperature ($T_c$) of PBD was detected on the cooling cycle of DSC and varied between 70 and 90° C. The melting points ($T_m$s) of Compounds 3–5 were determined to be about 320, 410 and 260° C., respectively, all higher than that of PBD. Exothermic on-set $T_c$s around 220, 200, and 210° C. were observed for Compounds 3–5, respectively. On-set decomposition temperatures ($T_d$s) determined by TGA varied between 400 and 500° C. depending on the substituent of 3–5 (see Table 1). These $T_d$s were all significantly higher than the $T_d$ of 308° C. for PBD. In addition, careful examination of DSC thermograms revealed that an endothermic step transition persistently appeared at about 97, 175 and 125° C., which was assigned to an on-set glass transition temperature for Compounds 3, 4 and 5, respectively. In general, DSC scans were performed at 10° C./min; on-set $T_g$s were determined by the intercept of the slope from the step-transition and the base line of prior-transition scans were marked on each thermogram. In contrast, no possible glass transition signal was detected for PBD in repeated heating-cooling DSC cycles. Thus, the tetraphenylmethane compounds described herein had enhanced $T_m$, $T_c$, $T_d$, and $T_g$ measurements.

TABLE 1

Absorptive, fluorescent, thermal, and redox properties of 3–5 and PBD

| Compound | $\lambda_a{}^a$ (nm) | $\lambda_f{}^a$ (nm) | $\Phi_F{}^b$ | $T_g{}^c$ (° C.) | $T_c{}^c$ (° C.) | $T_m{}^c$ (° C.) | $T_d{}^d$ (° C.) | $V_{red}(eV)^e$ Vs Ag/Ag |
|---|---|---|---|---|---|---|---|---|
| 3 | 315 | 386 | 0.9 | 97 | 227 | 337 | 428 | ~2.40 |
| 4 | 296 | 372 | 0.8 | 175 | 205 | 400 | 405 | –2.35~ –2.40 |
| 5 | 292 | 370 | 0.8 | 125 | 202 | 270 | 499 | –1.32, –2.25$^f$ |
| PBD | 303 | 361 | 0.8 | $^g$ | 70–90 | 137 | 308 | –2.37 |

$^a$Measured in ethyl acetate solution;
$^b$Fluorescent quantum yield determined relative to 2-phenyl-5-(4-biphenyl)-1,3,4-oxadiazole in benzene at 298 K ($\Phi_F$ = 0.8)10;
$^c$Determined by DSC with scanning rate of 10° C./min;
$^d$Determined by TGA with scanning rate of 10° C./min under nitrogen atmosphere;
$^e$Potential of the first reduction process in DMF solution, which was made with 0.1M in tetrabutylammonium perchlorate as the supporting electrolyte. Potential sweep rate was kept at 100 mV/s in all measurements;
$^f$Potential of the second reduction process;
$^g$not observed.

EXAMPLE 6

Preparation of Electroluminescence Devices Using CF3OXD (Compound 5)

A three-layer OLED device was constructed by vacuum deposition onto an indium-tin-oxide coated glass substrate. The device had the following layered structure: α-NPB (400 Å)/Alq(50 Å)/Compound 5(400 Å)/Mg:Ag. The compound α-NPB (N,N'-diphenyl-N,N'-bis(1-naphthyl)-1,1'-biphenyl-4,4"-diamine) served as the hole-transporting layer and Alq (tris(8-hydroxyquinoline) aluminum) served as the electroluminescent material. A similar OLED device made of α-NPB (400 Å)/Alq (50 Å)/PBD (400 Å)/Mg:Ag containing PBD as the electron-transporting layer was constructed for comparison.

All current, voltage, and luminescence measurements were performed with the devices exposed to air. Both OLED devices started glowing at 7~8 V applied bias voltage with green luminescence ($\lambda_f$~515 nm), a characteristic electroluminescence from an Alq lumophore. Differences between the two OLED devices were noted in terms of current-luminescence-voltage. Graphs showed that luminescence-current-voltage characteristics of the device ITO/α-NPB/Alq/PBD/Mg:Ag was different from those of the device ITO/α-NPB/Alq/Compound 5/Mg:Ag.

More specifically, the allowed current density (mA/cm²) in both devices was different. At a drive voltage of 12 V, the current was three times lower in the device containing Compound 5 than that containing PBD, indicating that there was higher current resistance in the device containing Compound 5 as the electron-transporting layer. Furthermore, the device containing Compound 5 was more than three times dimmer than the device containing PBD as ETL under the same drive voltage (10 V). Therefore, with smaller current density as well as weaker electroluminescence, the device containing Compound 5 still had a comparable maximum external quantum efficiency ~0.75% to ~1% (both occur at a drive voltage around 8 V) as the device containing PBD. More importantly, whereas the intensity of electroluminescence severely decreased at 12 V for the OLED device containing PBD, little deterioration was observed for the electroluminescence of the device containing Compound 5. With the drive voltage varying from 8 to 12 V, the external quantum efficiency dropped continuously from 0.75% to 0.60% (a 20% loss in external quantum efficiency) for the device containing Compound 5. There was a more than 70% loss in external quantum efficiency (from 1% to ca. 0.25%) for the device containing PBD in the same range of drive voltage.

EXAMPLE 7

Synthesis of Tetrakis(4-(5-(4-diphenylaminophenyl)-2-oxadiazolyl)phenyl)methane (p-TPAOXD)

Tetrakis(4-benzoyl chloride)methane was prepared by treating tetraphenylmethane-4,4',4'',4'''-tetracarboxylic acid with an excess of thionyl chloride. The compound p-tetrazolyltriphenylamine was prepared by the method of Tamoto et al. (N. Tamoto, C. Adachi, K. Nagai, "Electroluminescence of 1,3,4-oxadiazole and triphenylamine-containing molecules as an emitter in organic multilayer light emitting diodes", Chem. Mater. 9, pp. 1077–1085, 1997).

The tetrakis(4-benzoyl chloride)methane was then allowed to react with the p-tetrazolyltriphenylamine. The second bright green band (under long-wavelength UV light) that developed during flash column chromatography (silica gel, 19 part dicloromethane vs. 1 part ethyl acetate) was collected. Yield: 50% (0.78 g). $^1$H NMR (400 MHz, CDCl$_3$): δ [ppm] 8.06 (d, 8H, J=8.7 Hz), 7.90 (d, 8H, J=8.9 Hz), 7.45 (d, 8H, J=8.65 Hz), 7.27–7.33 (m, 16H), 7.14 (d, 16H, J=8.5 Hz), 7.06–7.12 (m, 16H). $^{13}$C{1H} NMR (100 MHz, CDCl$_3$): δ [ppm] 164.6, 163.3, 151.0, 148.4, 146.5, 131.3, 129.5, 127.9, 126.6, 125.6, 124.4, 122.6, 120.9, 115.7, 65.4. FAB-MS: calcd MW, 1564.58, m/e=1566 (M+1$^+$). Anal. Found (calcd) for C$_{105}$H$_{72}$N$_{12}$O$_4$ (p-TPAOXD): C, 80.40 (80.54); H, 4.80(4.63); N, 10.63(10.73).

EXAMPLE 8

Synthesis of m-TPAOXD

The synthesis of m-tetrazolyltriphenylamine was begun with the palladium-catalyzed amination of m-bromobenzyonitrile with diphenylamine. The resulting m-cyanotriphenylamine (isolated yield of 50%) was reacted with sodium azide and ammonium chloride, and then acidified with aqueous hydrochloric acid to precipitate the product m-tetrazolyltriphenylamine.

Tetrakis(4-benzoyl chloride)methane (prepared as described above) was then allowed to react with the m-tetrazolyltriphenylamine.

The product m-TPAOXD was purified by column chromatography and was fully characterized by FAB-MS, $^1$H and $^{13}$C NMR spectroscopies and elemental analysis. The characterized data were consistent with the proposed structure.

The syntheses of p-TPAOXD and m-TPAOXD are shown below in Schemes 2 and 3.

Scheme 2

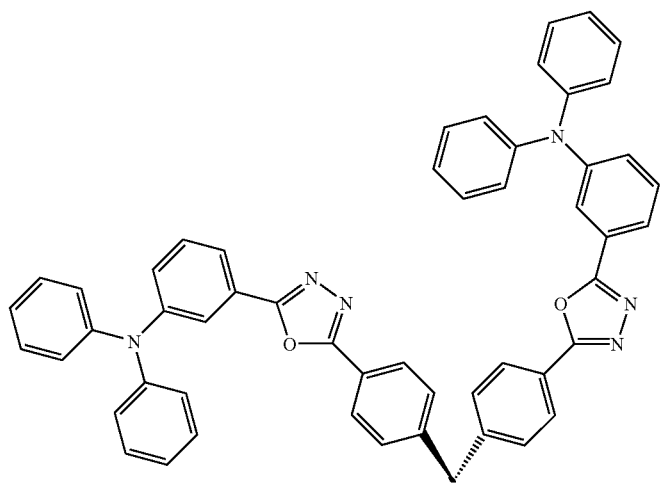

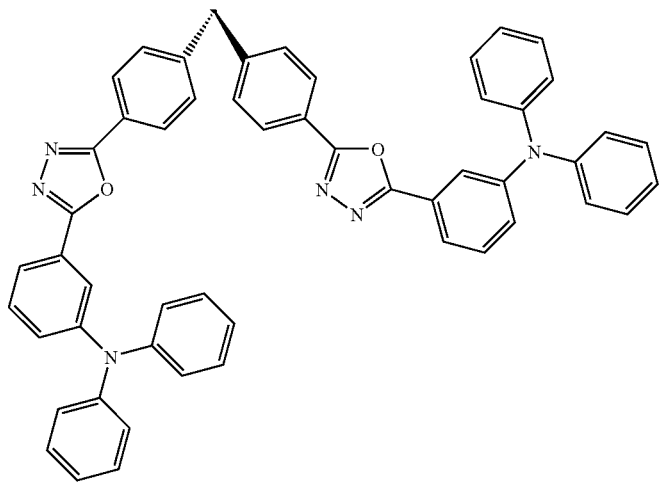
m-TPAOXD
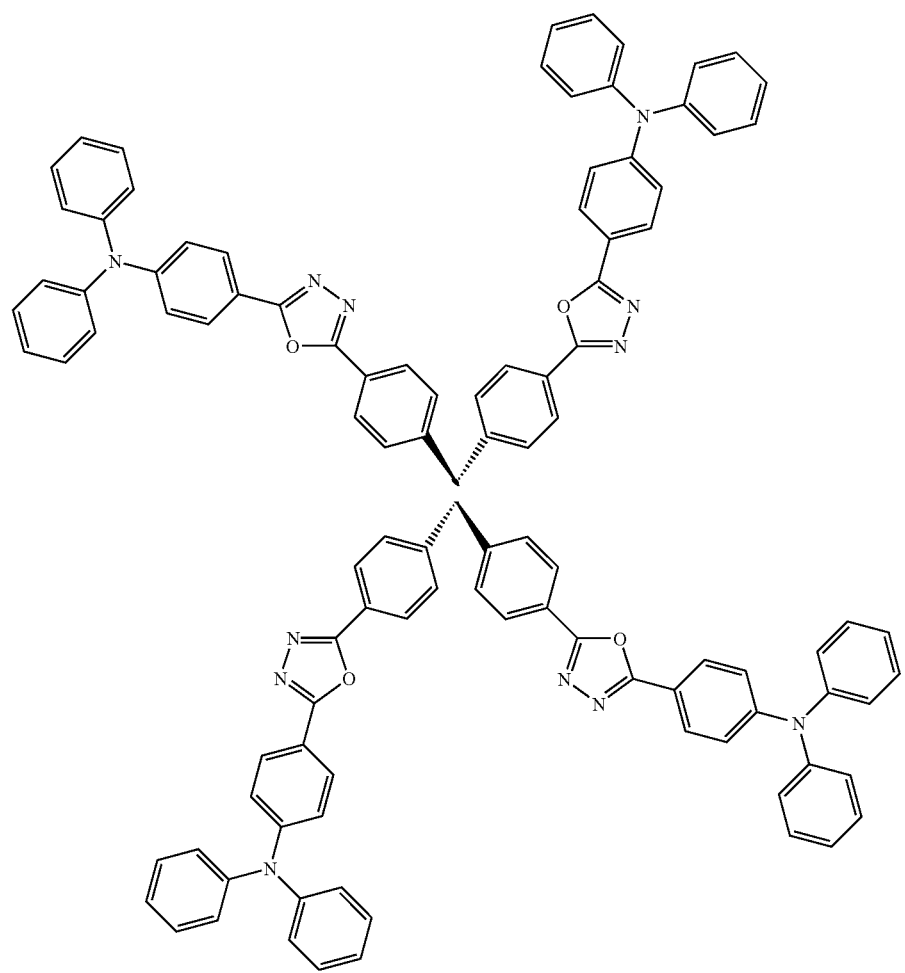
p-TPAOXD

Scheme 3

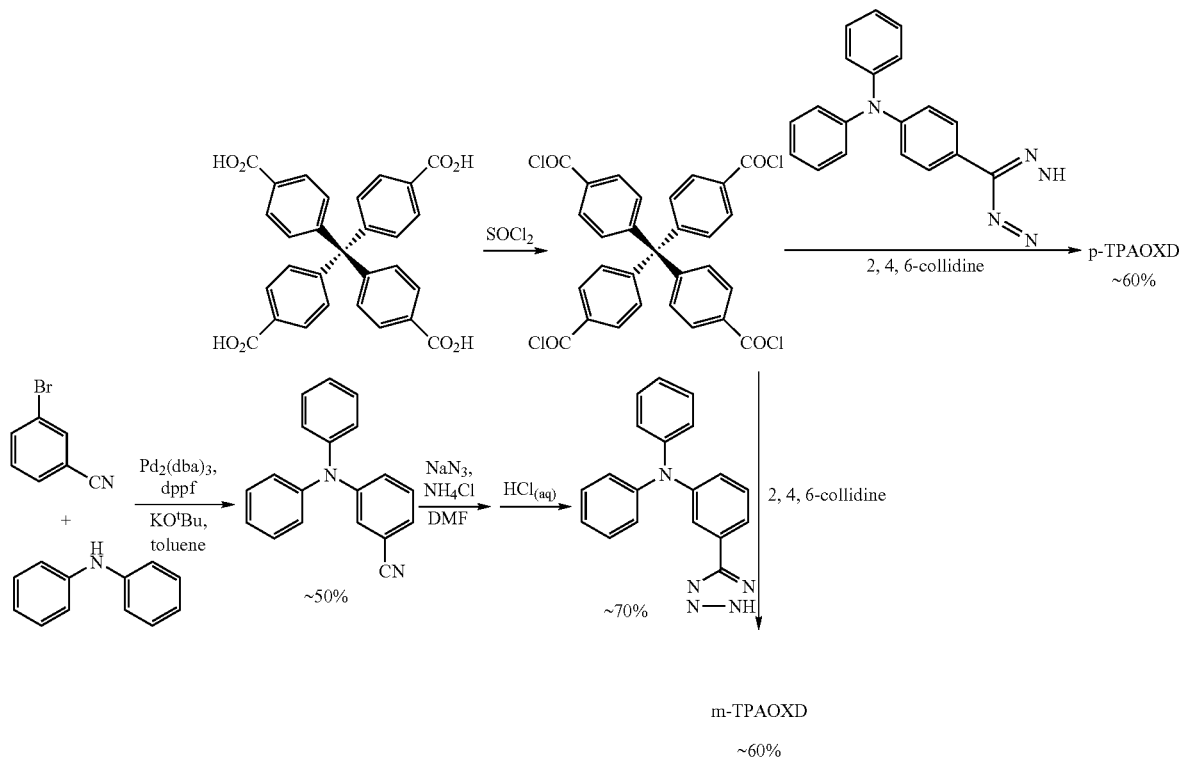

m-TPAOXD

~60%

EXAMPLE 9

Physical and Electronic Properties of p-TPAOXD and m-TPAOXD

Due to the different substitution position of the electron donating diphenylamino group on the 2,3-diphenyl-1,3,4-oxadiazole, there were some interesting features on the absorption and fluorescence spectra of m-TPAOXD and p-TPAOXD. Absorption spectra and fluorescence spectra of m-TPAOXD and p-TPAOXD were determined. The relative intensities of the fluorescence spectra were scaled based on the fluorescence quantum efficiencies of m-TPAOXD and p-TPAOXD. The compound p-TPAOXD had two major absorption bands at 287 and 366 nm with extinction coefficients near and over $10^5$, respectively. However, m-TPAOXD showed only one major absorption band at 298 nm with an accompanying shoulder at about 320 nm as well as a weak and broad absorption band around 365 nm. The absorption band with a maximum at 366 of p-TPAOXD may be attributed to the charge transfer absorption band due to the p-conjugation between the triphenyl amine and oxadiazole units that is lacking in meta-substituted m-TPAOXD. The fluorescence intensity of p-TPAOXD (fluorescence quantum yield ~50%) was about six times stronger than that of m-TPAOXD (fluorescence quantum yield ~9%); this phenomenon is probably due to the conjugated para-substution of the π-excessive/π-deficient moiety in p-TPAOXD. Since p-TPAOXD showed similar excitation and absorption spectra, both absorption bands of p-TPAOXD may contribute to the fluorescence with an emission maximum around 450 mn. Further, similar excitation and absorption spectra of p-TPAOXD in dichloromethane were also observed.

In addition, the photoluminescence spectra of p-TPAOXD in solution and as a solid film were compared. The emission difference was relatively small and the emission maximum was 19 nm red shifted from solution to solid film. Besides, p-TPAOXD had a similar emission bandwidth in solution and as a solid film. Both a similar bandwidth and a small emission band shift from solution spectra to solid film spectra were indicative of negligible excimer formation in the solid state, which in turn implied a homogeneous amorphous film with limited intermolecular contact.

The amorphous glass-forming natures of both m-TPAOXD and p-TPAOXD were fully revealed by differential scanning calorimetry (DSC). Repeated DSC heating and cooling (10° C./min) scan cycles on a sample of p-TPAOXD were determined. It was evident that the sample of p-TPAOXD showed only an endothermic step-like transition around 190° C. that was assigned to the $T_g$ of p-TPAOXD (on-set $T_g$ was estimated to be about 187° C.). No indication of $T_c$ or $T_m$ could be located from the DSC thermograms (scan temperatures between 40 and 400° C.) of p-TPAOXD. The thermal behavior of the phase transition of p-TPAOXD was similar to that of a polymer sample. The DSC thermogram of m-TPAOXD was similar to that of p-TPAOXD but the on-set $T_g$ was located at about 149° C. (Table 2). Both m-TPAOXD and p-TPAOXD were thermally robust and their TGA (thermolgravimetric analysis) determined on-set $T_d$s were 464 and 474° C., respectively (Table 2).

The redox potentials of both m-TPAOXD and p-TPAOXD were determined by cyclic voltammetry; they were similar. Within the variation of measured potential of about ±50 mV, both compounds had similar first oxidation potentials around 0.75 V and first reduction potentials around −2.20 V (Table 2). These numbers imply that both m-TPAOXD and p-TPAOXD had a significantly lower HOMO (highest occupied molecular orbital) energy levels relative to that of α-NPD ($E^{OX}$=0.43 V vs. Ag/Ag$^+$), but LUMO (lowest unoccupied molecular orbital) energy levels comparable with that of BBOXD ($E^{red}$=−2.28 V vs. Ag/Ag$^+$). α-NPD is a triarylamine derivative and BBOXD is a 1,5 diaryl-substituted 1,3,4-oxadiazole derivative; both are widely used as hole transporting materials and electron transporting (hole blocking) materials, respectively, in OLEDs.

characterized in a number of ways. For example, the dependence of the electroluminescence (EL) and the wavelength was observed. More specifically, the emission maximum (~500 nm) of the electroluminescence spectrum of p-TPAOXD was about 20~30 nm red-shifted compared to its photoluminescence spectra. In addition, a weaker luminescence band with longer wavelength at about 650 nm was discernable; this band was probably due to the excimer formation of p-TPAOXD, even though there was no evidence of excimer formation from the photoluminescence spectra. The devices showed sky blue colors of luminescence at low applied voltages, but greenish white colors at elevated applied voltages; this phenomenom was due to the broad electroluminescence spectra of p-TPAOXD.

Further, the relationship between electrical current density (mA/cm$^2$) and applied voltage (V) was determined. In particular, the relationship between luminous efficiency (lm/W)/brightness (cd/m$^2$) and the applied voltage (V) was established. The devices described herein started glowing with a turn-on voltage about 7 or 8 V. However, the level of allowed current did not really take off until 10 or 11 V, indicating an imbalance between the holes and the electrons within the p-TPAOXD material. The unbalanced charge behavior gave the single-layer device limited luminous efficiency (~0.2 lm/W at a current density of 6~9 mA/cm$^2$). The brightness of the device could reach the maximum of 1690 cd/cm$^2$, but only under a relatively high driving voltage (14 V). The performance of the p-TPAOXD-containing single-layer devices can be optimized with better

TABLE 2

Optical, electrochemical, and thermal properties of m-TPAOXD and p-TPAOXD

| | $\lambda_{max}^{abs\ a}$ (nm) | log ε | $\lambda_{max}^{em}$ solution$^a$ (nm) | $\lambda_{max}^{em}$ solid film (nm) | $\Phi_f^b$ solution | $E^{ox}$vs. Ag/Ag$^{+c}$ V | $E^{red}$vs. | $T_g^d$ °C. | $T_d^e$ °C. |
|---|---|---|---|---|---|---|---|---|---|
| m-TPAOXD | 298 | 5.29 | 463 | 451 | 0.09 | 0.73 | −2.24 | 149 | 464 |
| p-TPAOXD | 287, 366 | 4.96, 5.16 | 448 | 467 | 0.50 | 0.76 | −2.18 | 187 | 474 |

$^a$In dichloromethane;
$^b$Fluorescent quantum yield determined relative to 2-phenyl-5-(4-biphenyl)-1,3,4-oxadiazole (PBOXD) in benzene ($\Phi_f$ = 0.8)27 for m-TPAOXD for p-TPAOXD at 298 K;
$^c$Potential of the first oxidation and reduction process in DMF solution, which was made with 0.1M in tetrabutylammonium perchlorate as the supporting electrolyte. Potential sweep rate was kept at 1000 mV/s in all measurements;
$^d$On-set glass transition temperatures determined by DSC under nitrogen with a scanning rate of 10° C./min;
$^e$On-set thermal decomposition temperatures determined by TGA under nitrogen with a scanning rate of 10° C./min.

EXAMPLE 10

Synthesis of Electroluminscence Device Using p-TPAOXD

The strongly fluorescent glassy p-TPAOXD was used to fabricate single-layer light-emitting devices. Layers of p-TPAOXD (~100 nm) were formed by spin-casting from tetrahydofuran solution (15 mg/mL) onto indium tin oxide (ITO) coated glass substrates. A calcium cathode was thermally deposited on the p-TPAOXD thin film followed by the deposition of silver metal as the top layer. The devices were control on the film thickness of p-TPAOXD by blending a tetraphenylmethane-based hole-blocking material into p-TPAOXD to balance the carried charges.

EXAMPLE 11

Syntheses of Other Tetrahedral Compounds

Representative syntheses of other tetrahedral compounds are summarized below in Schemes 4 and 5. These compounds are also useful in electroluminescence devices.

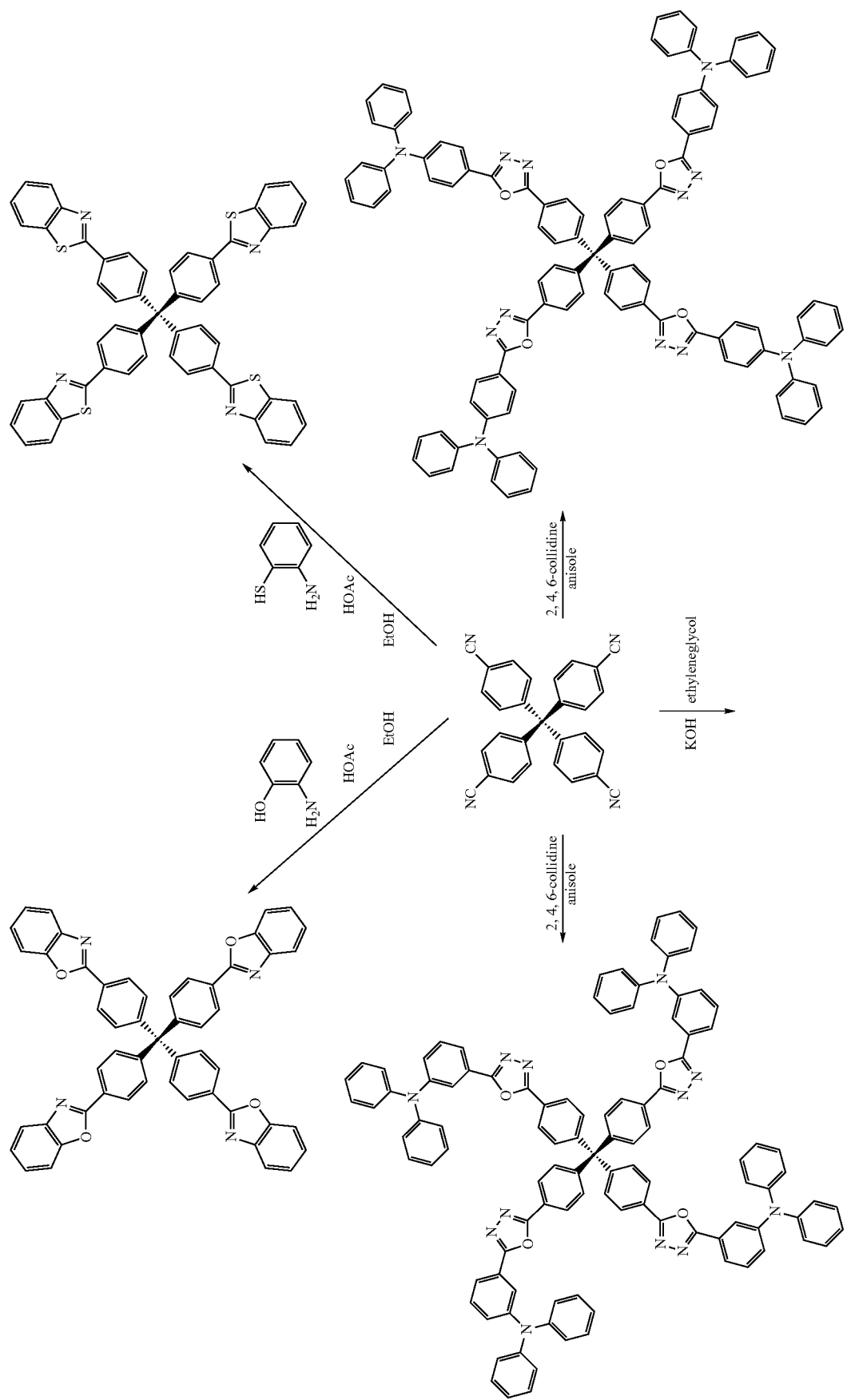
Scheme 4

-continued
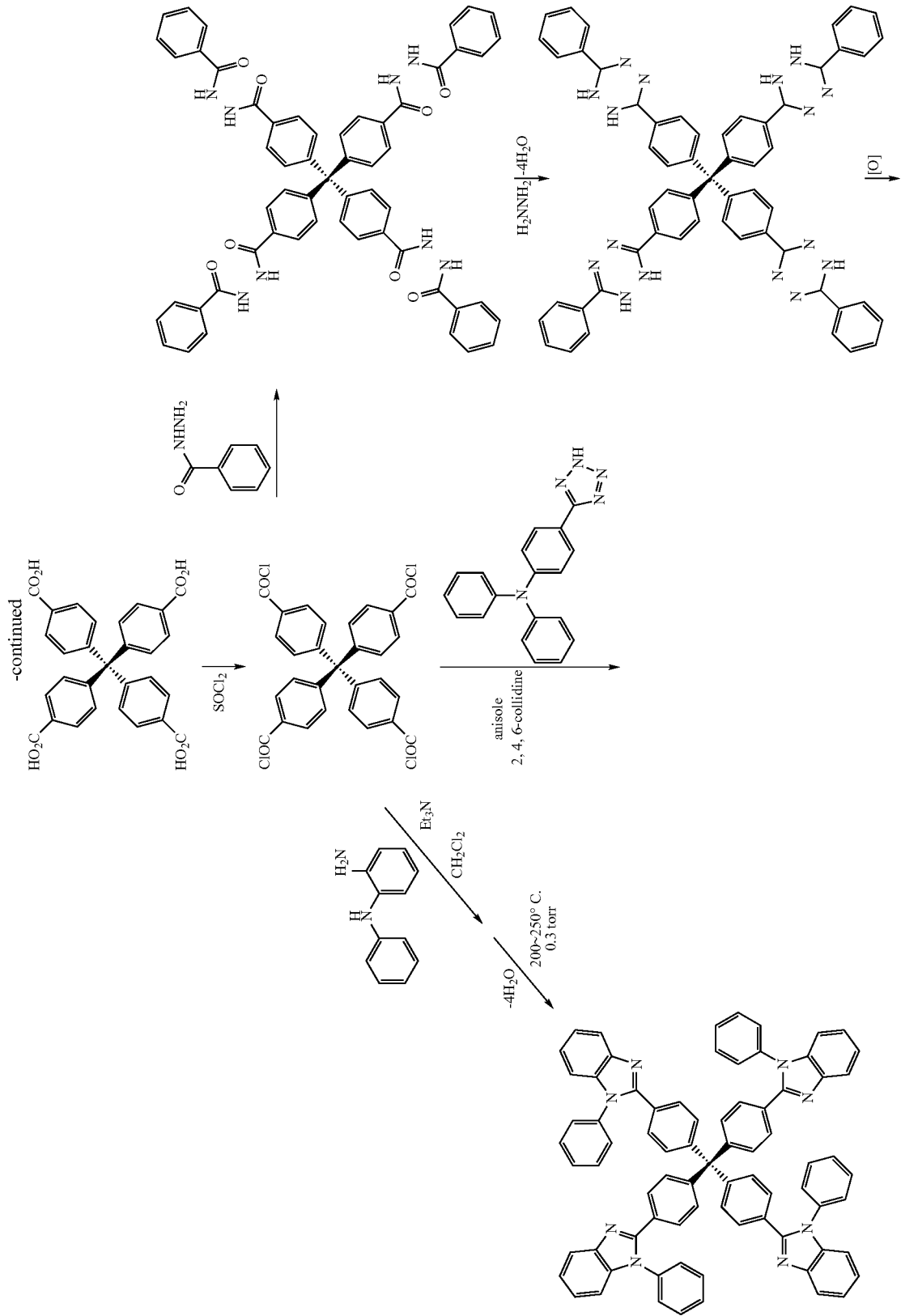

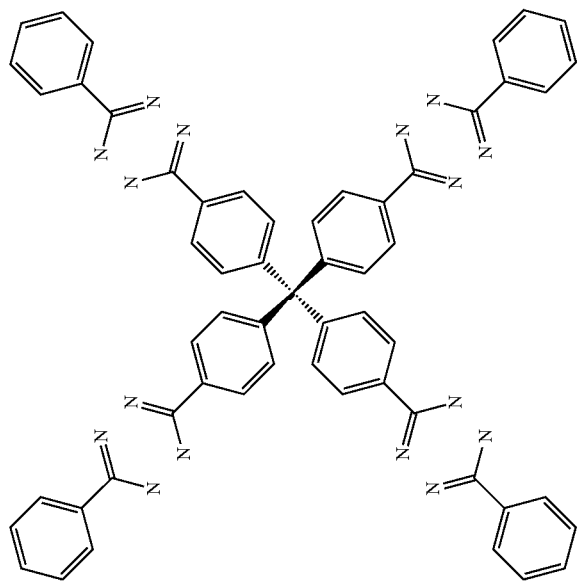
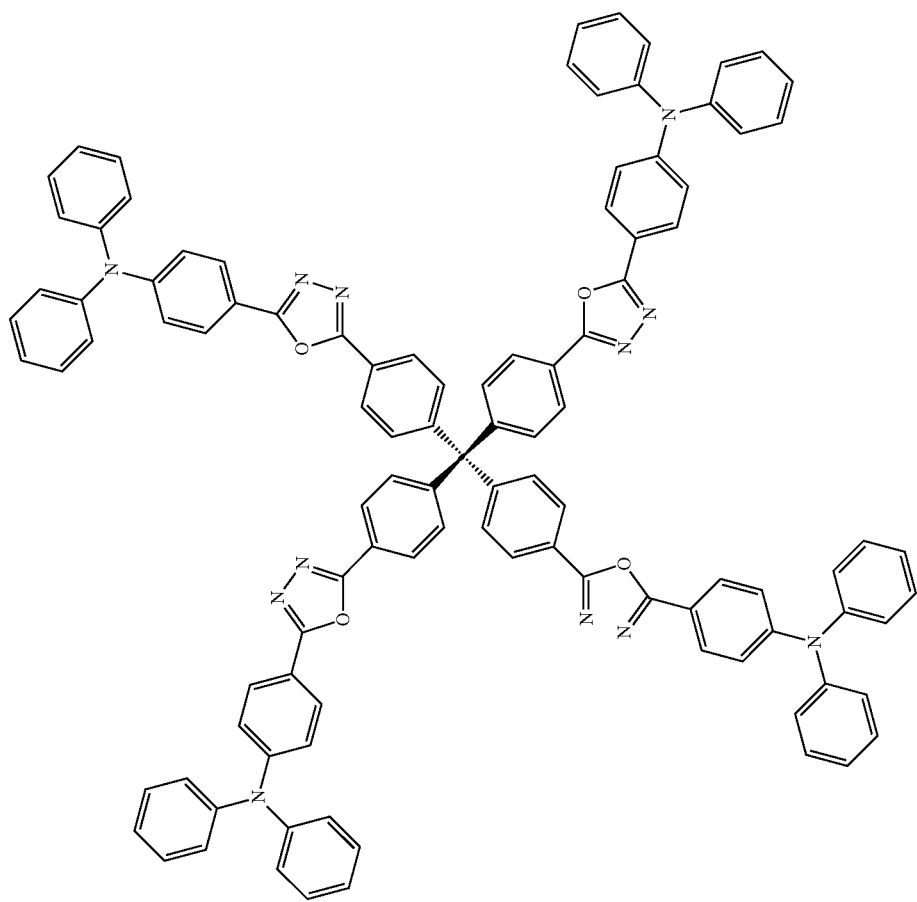

Scheme 5

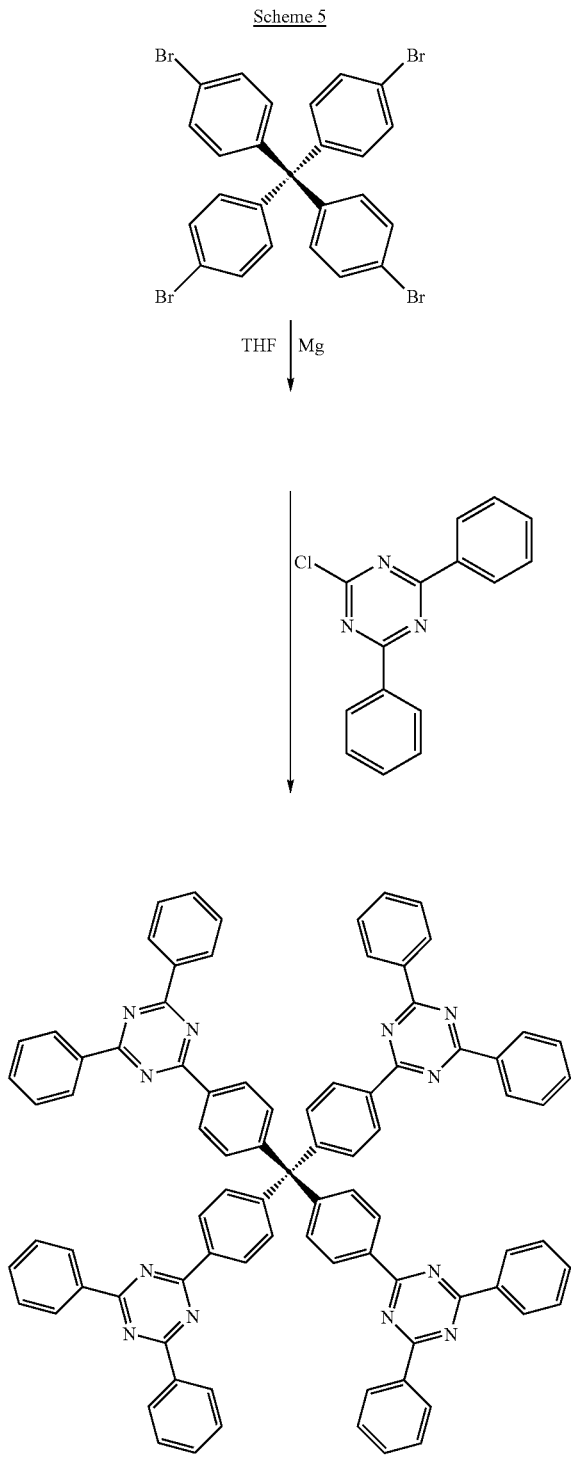

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Accordingly, other embodiments are within the scope of the following claims.

What is claimed is:

1. A compound of the following formula:

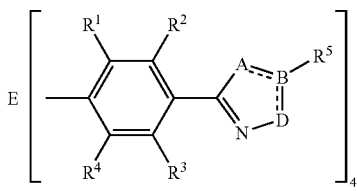

wherein each of $R^1$–$R^4$ is, independently, H, substituted or unsubstituted $C_{1-6}$ alkyl, OH, $C_{1-6}$ alkoxy, $N(R^6)(R^7)$, in which each of $R^6$ and $R^7$ is, independently, H or substituted or unsubstituted $C_{1-6}$ alkyl, $NO^2$, CN, or $CO_2R^8$, in which $R^8$ is H or $C_{1-6}$ alkyl; and wherein $R^5$ is H, substituted or unsubstituted $C_{1-6}$ alkyl, substituted or unsubstituted $C_{2-6}$ alkenyl, substituted or unsubstituted $C_{2-6}$ alkynyl, unsubstituted $C_{6-20}$ aryl or $C_{6-20}$ aryl substituted with OH, $C_{1-6}$ alkoxy or $N(R^{26})(R^{27})$; alkylaryl in which the aryl moiety is substituted with one or more $C_{1-6}$ alkyl groups further substituted with hydroxyl, protected hydroxyl, amino, protected amino, carboxy, protected carboxy, alkoxy, halo, CN, or $NO_2$, substituted or unsubstituted $C_{4-20}$ heteroaryl, $C_{10-20}$ diarylaminoaryl, or is absent, or B and D, together with $R^5$ and $R^{11}$, are substituted or unsubstituted aryl; in which each of $R^{26}$ and $R^{27}$ is, independently, H, substituted or unsubstituted $C_{1-6}$ alkyl, substituted or unsubstituted aryl, substituted or unsubstituted alkylaryl, $NO_2$, CN, or $CO_2R^{28}$, in which $R^{28}$ is H or $C_{1-6}$ alkyl;

wherein A is O, S, $N(R^9)$ in which $R^9$ is absent, H, substituted or unsubstituted alkyl, or substituted or unsubstituted aryl, N=N, or N=$C(R^{10})$ in which the C is adjacent to B and in which $R^{10}$ is substituted or unsubstituted alkyl, or substituted or unsubstituted aryl;

wherein B is C or N;

wherein D is N, NH, or $C(R^{11})$ in which $R^{11}$ is substituted or unsubstituted alkyl, or substituted or unsubstituted aryl, or B and D, together with $R^5$ and $R^{11}$ are substituted or unsubstituted aryl;

and wherein E is C or Si;

provided that when A is O and D is N, then B is C and the floating double bond is between B and D;

further provided that when A is $N(R^9)$ and $R^9$ is absent, then B is N, $R^5$ is absent, D is NH, and the floating double bond is between A and B;

further provided that when A is N=N, then B is C, D is N, and the floating double bond is between B and D;

further provided that when A is N=$C(R^{10})$, then B is N, $R^5$ is absent, D is $C(R^{11})$, and the floating double bond is between B and D;

further provided that when A is $N(R^9)$ and $R^9$ is H, alkyl, or aryl, then B is C, D is $C(R^{11})$, and the floating double bond is between B and D; and further provided that when A is O or S and D is $C(R^{11})$, then B is C and the floating double bond is between B and D.

2. The compound of claim 1, wherein A is O.

3. The compound of claim 2, wherein each of $R^1$–$R^4$ is H.

4. The compound of claim 2, wherein $R^5$ is unsubstituted $C_{6-20}$ aryl or $C_{6-20}$ aryl substituted with OH, $C_{1-6}$ alkoxy or $N(R^{26})(R^{27})$; or alkylaryl in which the aryl moiety is substituted with one or more $C_{1-6}$ alkyl groups further substituted with hydroxyl, protected hydroxyl, amino, protected amino, carboxy, protected carboxy, alkoxy, halo, CN, or $NO_2$; in which each of $R^{26}$ and $R^{27}$ is, independently, H, substituted or unsubstituted $C_{1-6}$ alkyl, substituted or unsubstituted aryl, substituted or unsubstituted alkylaryl, $NO_2$, CN, or $CO_2R^{28}$, in which $R^{28}$ is H or $C_{1-6}$ alkyl.

5. The compound of claim 4, wherein $R^5$ has the following formula:

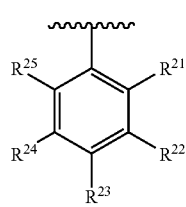

wherein each of $R^{21}$–$R^{25}$ is, independently, H, $C_{1-6}$ alkyl groups further substituted with hydroxyl, protected hydroxyl, amino, protected amino, carboxy, protected carboxy, alkoxy, halo, CN, or $NO_2$; OH, $C_{1-6}$ alkoxy, $N(R^{26})(R^{27})$, in which each of $R^{26}$ and $R^{27}$ is, independently, H, substituted or unsubstituted $C_{1-6}$ alkyl, substituted or unsubstituted aryl, substituted or unsubstituted alkylaryl, $NO_2$, CN, or $CO_2R^{28}$, in which $R^{28}$ is H or $C_{1-6}$ alkyl.

6. The compound of claim 5, wherein each of $R^{21}$–$R^{25}$ is, independently, H or methoxy.

7. The compound of claim 5, wherein each of $R^{21}$–$R^{25}$ is, independently, H or trifluoromethyl.

8. The compound of claim 1, wherein the compound has the following formula:

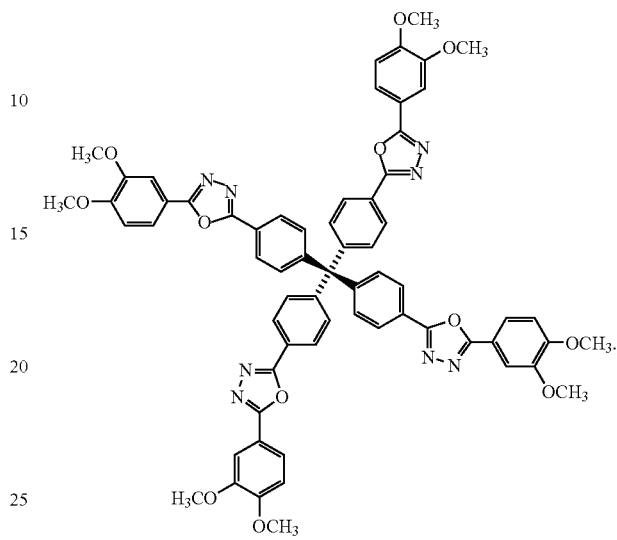

9. The compound of claim 1, wherein the compound has the following formula:

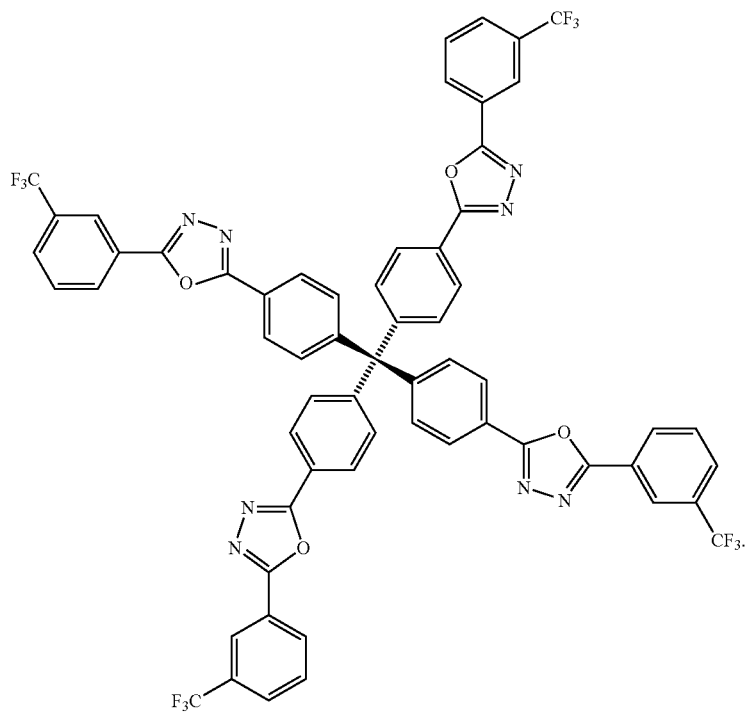

10. The compound of claim 1, wherein A is $N(R^9)$, in which $R^9$ is absent.

11. The compound of claim 10, wherein the compound has the following formula:

12. The compound of claim 1, wherein the compound has the following formula:

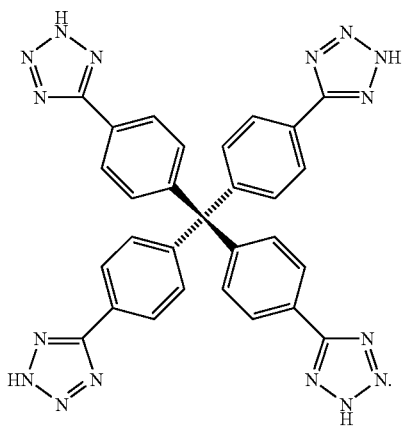

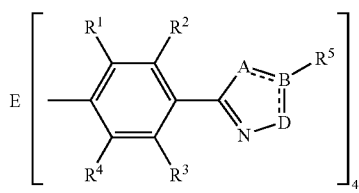

wherein each of $R^1$–$R^4$ is, independently, H, substituted or unsubstituted $C_{1-6}$ alkyl, OH, $C_{1-6}$ alkoxy, $N(R^6)(R^7)$, in which each of $R^6$ and $R^7$ is, independently, H or substituted or unsubstituted $C_{1-6}$ alkyl, $NO_2$, CN, or $CO_2R^8$, in which $R^8$ is H or $C_{1-6}$ alkyl; and wherein $R^5$ is H, substituted or unsubstituted $C_{1-6}$ alkyl, substituted or unsubstituted $C_{2-6}$ alkenyl, substituted or unsubstituted $C_{2-6}$ alkynyl, unsubstituted $C_{6-20}$ aryl or $C_{6-20}$ aryl substituted with OH, $C_{1-6}$ alkoxy or $N(R^{26})(R^{27})$; alkylaryl in which the aryl moiety is substituted with one or more $C_{1-6}$ alkyl groups further substituted with hydroxyl, protected hydroxyl, amino, protected amino, carboxy, protected carboxy, alkoxy, halo, CN, or $NO_2$, substituted or unsubstituted $C_{4-20}$ heteroaryl, $C_{10-20}$ diarylaminoaryl, or is absent, or B and D, together with $R^5$ and $R^{11}$, are substituted or unsubsti-

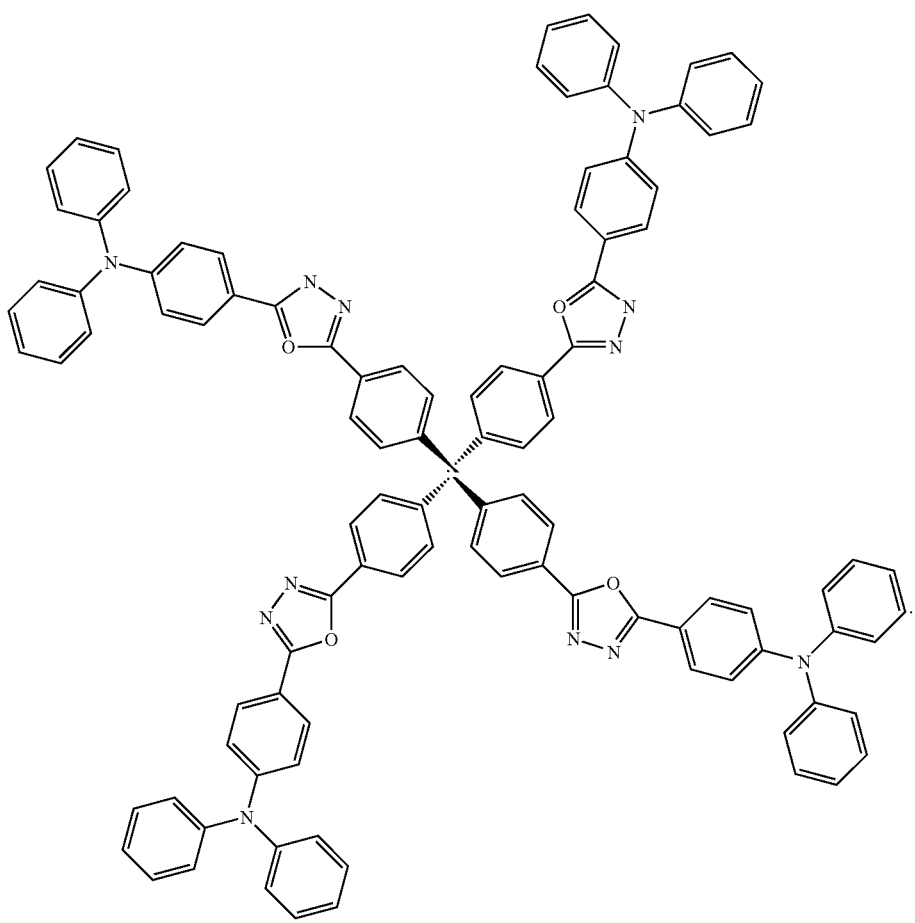

13. An electroluminescence device comprising a substrate, a hole transporting layer, and emitting layer, and an electron transporting layer, wherein at least one of the hole transporting layer, the emitting layer, and the electron transporting layer comprises a compound having the following formula:

tuted aryl; in which each of $R^{26}$ and $R^{27}$ is, independently, H, substituted or unsubstituted $C_{1-6}$ alkyl, substituted or unsubstituted aryl, substituted or unsubstituted alkylaryl, $NO_2$, CN, or $CO_2R^{28}$, in which $R^{28}$ is H or $C_{1-6}$ alkyl;

wherein A is O, S, $N(R^9)$ in which $R^9$ is absent, H, substituted or unsubstituted alkyl, or substituted or unsubstituted aryl, N=N, or $N=C(R^{10})$ in which the C is adjacent to B and in which $R^{10}$ is substituted or unsubstituted alkyl, or substituted or unsubstituted aryl;

wherein B is C or N;

wherein D is N, NH, or $C(R^{11})$ in which $R^{11}$ is substituted or unsubstituted alkyl, or substituted or unsubstituted aryl, or B and D, together with $R^5$ and $R^{11}$ are substituted or unsubstituted aryl; and wherein E is C or Si;

provided that when A is O and D is N, then B is C and the floating double bond is between B and D;

further provided that when A is $N(R^9)$ and $R^9$ is absent, then B is N, $R^5$ is absent, D is NH, and the floating double bond is between A and B;

further provided that when A is N=N, then B is C, D is N, and the floating double bond is between B and D;

further provided that when A is $N=C(R^{10})$, then B is N, $R^5$ is absent, D is $C(R^{11})$, and the floating double bond is between B and D;

further provided that when A is $N(R^9)$ and $R^9$ is H, alkyl, or aryl, then B is C, D is $C(R^{11})$, and the floating double bond is between B and D; and further provided that when A is O or S and D is $C(R^{11})$, then B is C and the floating double bond is between B and D.

14. The device of claim 13, wherein A is O, B is C, and D is N.

15. The device of claim 14, wherein each of $R^1$–$R^4$ is H.

16. The device of claim 13, wherein the compound has the following formula:

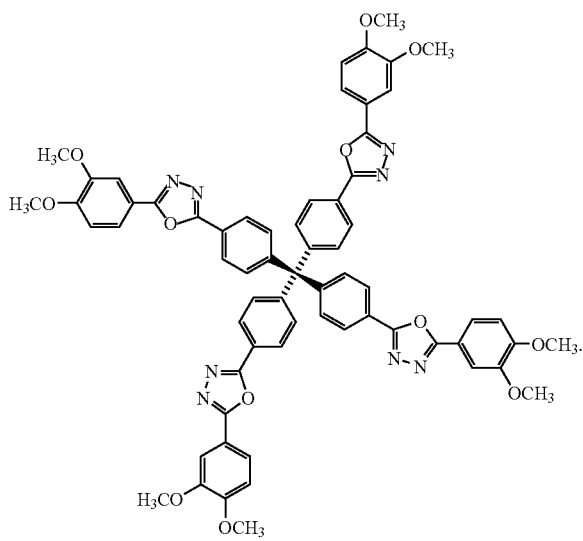

17. The device of claim 13, wherein the compound has the following formula:

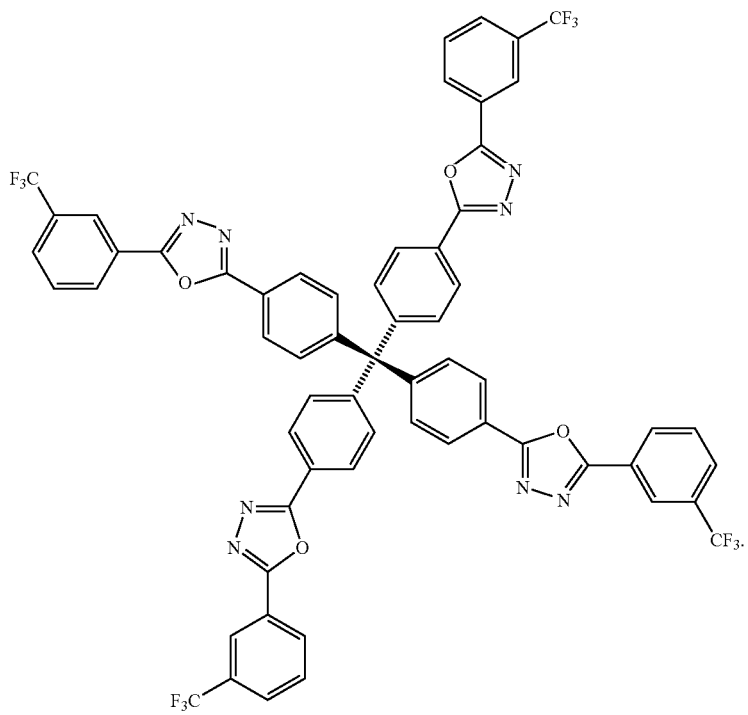

18. The device of claim 13, wherein the compound has the following formula:
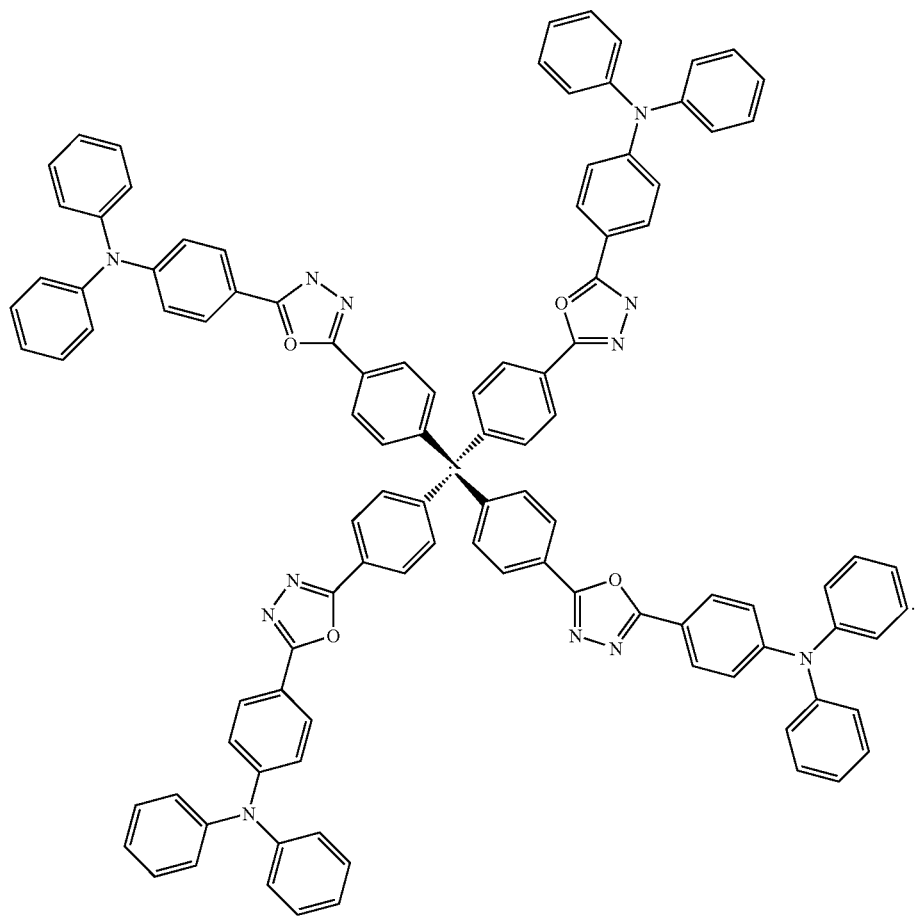
* * * * *